(12) United States Patent
Konawa

(10) Patent No.: US 10,813,800 B2
(45) Date of Patent: Oct. 27, 2020

(54) ABSORBENT ARTICLE

(71) Applicant: DAIO PAPER CORPORATION, Ehime (JP)

(72) Inventor: Satoko Konawa, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 299 days.

(21) Appl. No.: 15/781,279

(22) PCT Filed: Dec. 8, 2016

(86) PCT No.: PCT/JP2016/086600
§ 371 (c)(1),
(2) Date: Jun. 4, 2018

(87) PCT Pub. No.: WO2017/099186
PCT Pub. Date: Jun. 15, 2017

(65) Prior Publication Data
US 2018/0353353 A1 Dec. 13, 2018

(30) Foreign Application Priority Data
Dec. 9, 2015 (JP) .................................. 2015-240050

(51) Int. Cl.
*A61F 13/534* (2006.01)
*A61F 13/537* (2006.01)
(Continued)

(52) U.S. Cl.
CPC ...... *A61F 13/53756* (2013.01); *A61F 13/532* (2013.01); *A61F 13/533* (2013.01);
(Continued)

(58) Field of Classification Search
CPC ............... A61F 13/532; A61F 13/5323; A61F 13/53756; A61F 2013/53051;
(Continued)

(56) References Cited

U.S. PATENT DOCUMENTS 5,030,314 A * 7/1991 Lang ................. A61F 13/15634
156/390
5,486,167 A 1/1996 Dragoo et al.
(Continued)

FOREIGN PATENT DOCUMENTS

JP S61-000928 U 1/1986
JP 2007-244882 9/2007
(Continued)

OTHER PUBLICATIONS

International Search Report for PCT/JP2016/086600 dated Feb. 14, 2017.
(Continued)

*Primary Examiner* — Catharine L Anderson
(74) *Attorney, Agent, or Firm* — IPUSA, PLLC

(57) ABSTRACT

A polymer provided region (13) at which a superabsorbent polymer (12) is provided, and a polymer non-provided region (14) at which the superabsorbent polymer (12) is not provided are formed, a liquid diffusion sheet (15), that promotes diffusion of body fluid in a plane direction, is staked to be adjacent to a skin side surface of a lower layer sheet (11), and an upper layer sheet (10) is bonded with the liquid diffusion sheet (15) under a state that the upper layer sheet (10) contacts the liquid diffusion sheet (15), at the polymer non-provided region (14) to form a polymer sheet (4).

5 Claims, 9 Drawing Sheets

(51) Int. Cl.
*A61F 13/533* (2006.01)
*A61F 13/532* (2006.01)
*A61F 13/53* (2006.01)
*A61F 13/47* (2006.01)

(52) U.S. Cl.
CPC ........ *A61F 13/537* (2013.01); *A61F 13/5323* (2013.01); *A61F 13/53436* (2013.01); *A61F 2013/4708* (2013.01); *A61F 2013/530306* (2013.01); *A61F 2013/530562* (2013.01)

(58) Field of Classification Search
CPC ........ A61F 2013/530547; A61F 2013/530554; A61F 2013/530562; A61F 2013/53463
See application file for complete search history.

(56) References Cited

U.S. PATENT DOCUMENTS

| | | | |
|---|---|---|---|
| 5,938,650 A * | 8/1999 | Baer | A61F 13/5323 604/368 |
| 9,056,034 B2 * | 6/2015 | Akiyama | A61F 13/49473 |
| 9,295,593 B2 * | 3/2016 | Van Malderen | A61F 13/5323 |
| 9,517,169 B2 * | 12/2016 | Nakakado | A61F 13/539 |
| 9,532,909 B2 * | 1/2017 | Umebayashi | A61F 13/5323 |
| 2004/0054344 A1 | 3/2004 | Roettger et al. | |
| 2006/0069375 A1 | 3/2006 | Waksmundzki et al. | |
| 2007/0156108 A1 | 7/2007 | Becker et al. | |
| 2008/0119810 A1 | 5/2008 | Kuroda et al. | |
| 2011/0060303 A1 | 3/2011 | Bissah et al. | |
| 2012/0226253 A1 | 9/2012 | Urushihara | |
| 2016/0151213 A1 * | 6/2016 | Bauduin | A61L 15/58 604/365 |
| 2016/0250083 A1 * | 9/2016 | Tsujimoto | B29C 66/433 604/385.01 |

FOREIGN PATENT DOCUMENTS

| | | |
|---|---|---|
| JP | 2008-125917 | 6/2008 |
| JP | 2011-136077 | 7/2011 |
| JP | 2014-117472 | 6/2014 |
| WO | 2003/061524 | 7/2003 |
| WO | 2012/170778 | 12/2012 |
| WO | 2013/184859 | 12/2013 |
| WO | 2015/095003 | 6/2015 |
| WO | 2015/095514 | 6/2015 |

OTHER PUBLICATIONS

Extended European search report for European Patent Application No. 16873079.4 dated Aug. 13, 2018.

* cited by examiner (S)

ABSORBENT ARTICLE

BACKGROUND OF THE INVENTION

The present invention relates to an absorbent article used in sanitary napkins, panty liners, incontinence pads and the like, and more in detail, to an absorbent article including a polymer sheet in which a superabsorbent polymer is provided between an upper layer sheet and a lower layer sheet.

Description of the Related Art

Conventionally, as absorbent articles, a structure is known in which an absorbent body having a function to absorb and keep body fluid is provided between a liquid impermeable backsheet such as a polyethylene sheet or a polyethylene sheet laminate non-woven-fabric, and a liquid permeable topsheet such as a non-woven-fabric or a liquid permeable plastic sheet.

After various improvements on such kinds of absorbent articles, a structure is suggested as an absorbent body including a polymer sheet in which a superabsorbent polymer is provided between two sheets. The polymer sheet has an advantage in absorbing and keeping a large amount of body fluid. However, as a superabsorbent polymer assembly in a powder form is included inside, the body fluid does not easily enter inside the polymer assembly, and there is a problem that the body fluid flows near a surface of the polymer assembly and is absorbed only by the superabsorbent polymer near the surface.

For example, Patent Documents 1 to 3 each discloses an absorbent article using such a polymer sheet. Patent Document 1 discloses an absorbent article including an upper sheet-like absorbent layer, a fiber assembly layer and a lower sheet-like absorbent layer in this order from a topsheet side, wherein each of the upper sheet-like absorbent layer and the lower sheet-like absorbent layer includes absorbent resin but does not include a pulp fiber between non-woven-fabric sheets and includes a plurality of absorbent resin existing regions in each of which the absorbent resin is provided and absorbent resin non-existing regions adjacent to the absorbent resin existing regions between the non-woven-fabric sheets, and wherein the non-woven-fabric sheets are bonded to form sealed portions at the absorbent resin non-existing regions.

Patent Document 2 discloses an absorbent article in which an absorbent core is constituted by a matrix layer (100) made of a non-woven-fabric, an absorbent polymer material layer (110), a fiber thermoplastic material layer (120) and a cover layer (130) made of a non-woven-fabric, wherein the absorbent polymer material layer is provided as a discontinuous layer so that a part of a surface of the matrix layer is not covered by the absorbent polymer material, and wherein the fiber thermoplastic material layer is placed on the absorbent polymer material layer to directly contact a surface of the absorbent polymer material layer, and also directly contact a surface of the matrix layer that is not covered by the absorbent polymer material so that the fiber thermoplastic material layer has a wavy shape over the surface of the absorbent polymer material and the surface of the matrix layer (paragraphs [0039] to [0046] and FIG. 4).

Patent Document 3 discloses an absorbent article including an absorbent body having a structure in which an absorbent polymer (3) is provided between a first sheet (1) and a second sheet (2), wherein the first sheet has an uneven surface having first protruding portions (11) and second protruding portions (12), wherein the second sheet has an uneven surface having third protruding portions (23) and fourth protruding portions (24), wherein the first sheet and the second sheet have the same frequency in unevenness, wherein the third protruding portions respectively enter inner spaces of the first protruding portions and partially bonded and fixed, wherein the second protruding portions respectively enter inner spaces of the fourth protruding portions while partially leaving inner spaces, wherein the absorbent polymer is filled in the inner spaces of the fourth protruding portions while leaving gap portions at a second protruding portion side, and wherein a fourth sheet (9) is stacked on a non-skin surface side of the second sheet (claim 1, paragraph [0066] and FIG. 7(B)).

Patent Documents

Patent Document 1: Japanese Patent No. 5318747
Patent Document 2: Japanese Laid-open Patent Publication No. 2007-244882
Patent Document 3: Japanese Laid-open Patent Publication No. 2014-117472

According to the absorbent article disclosed in Patent Document 1, as the non-woven-fabric sheets are bonded at the absorbent resin non-existing regions, it is possible to diffuse the body fluid at these regions in a plane direction. However, if diffusion rate of the non-woven-fabric sheets are low, the body fluid is absorbed by the absorbent resin near a discharging position, and an absorption efficiency may be lowered or fit may be worsened due to increasing in thickness as the absorbent resin at a specific portion is largely swelled.

Further, according to Patent Document 2 or 3, a technique to stack a sheet material separately provided from two sheets that seal the superabsorbent polymer therein is disclosed. However, if diffusion rate of the separately provided sheet material is low, similarly as described above, an absorption efficiency may be lowered or fit may be worsened.

SUMMARY OF THE INVENTION

Thus, the present invention is made in light of the above problems, and provides an absorbent article capable of efficiently absorbing body fluid and preventing worsening of fit due to increasing in thickness caused by swelling of a superabsorbent polymer when absorbing the body fluid.

According to an embodiment, there is provided an absorbent article including a polymer sheet in which a superabsorbent polymer is provided between an upper layer sheet provided at a skin side, and a lower layer sheet provided at a non-skin side, wherein a polymer provided region at which the superabsorbent polymer is provided, and a polymer non-provided region at which the superabsorbent polymer is not provided are formed in the polymer sheet, wherein a liquid diffusion sheet, that promotes diffusion of body fluid in a plane direction, is staked stacked to be adjacent to a skin side surface of the lower layer sheet, and wherein the upper layer sheet is bonded with the liquid diffusion sheet under a state that the upper layer sheet contacts the liquid diffusion sheet, at the polymer non-provided region.

As described above in detail, according to the invention, it is possible to efficiently absorb body fluid, and also it is possible to prevent worsening of fit due to increasing in thickness by swelling of a superabsorbent polymer when absorbing the body fluid.

DETAILED DESCRIPTION OF THE PREFERRED EMBODIMENTS

In the following, embodiments of the present invention are described with reference to the accompanying drawings. In the following, an example is described in which a sanitary napkin is used as an absorbent article.

(Basic Structure of Sanitary Napkin 1)

Figure 1:
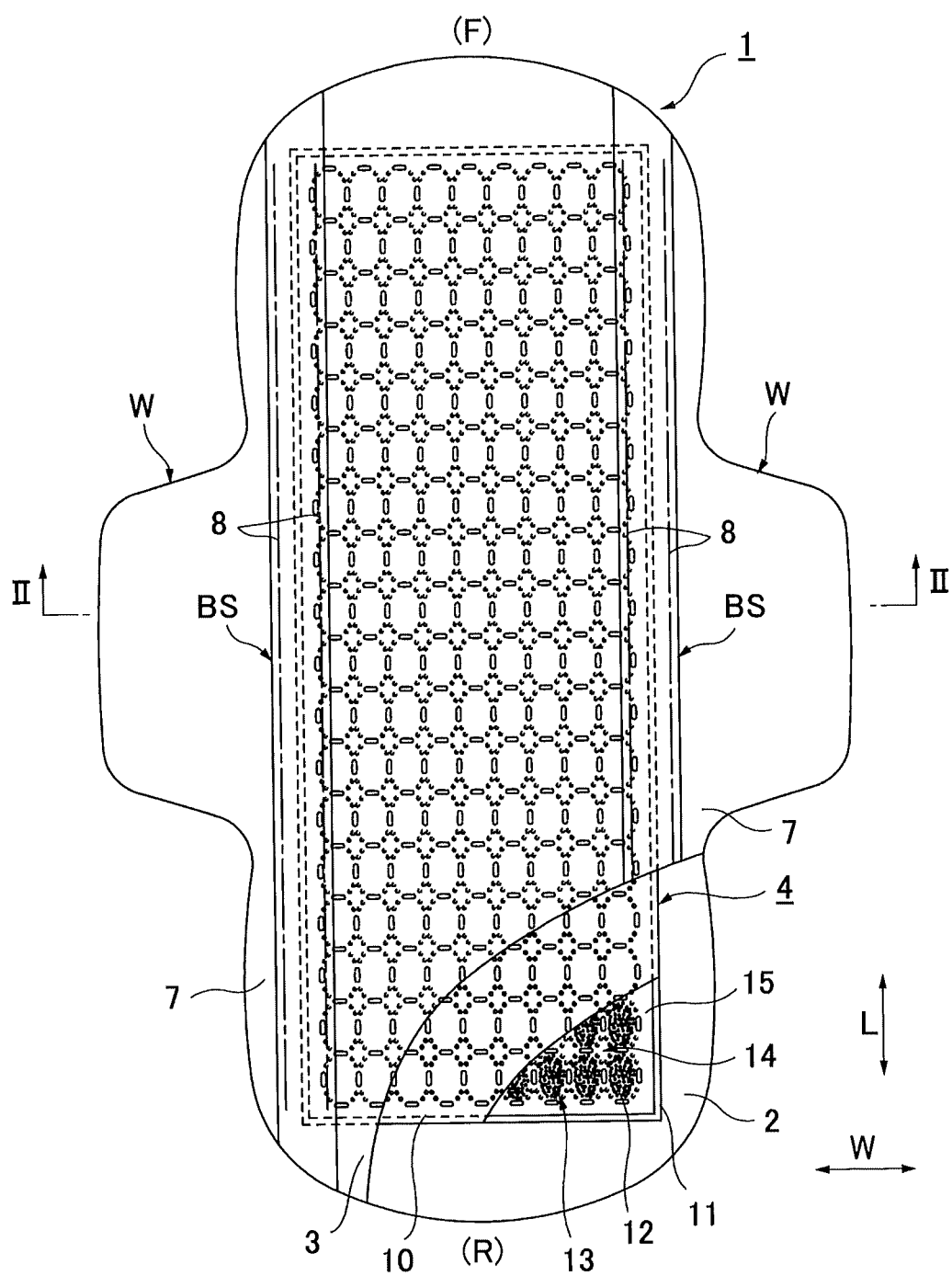
FIG. 1 is a partial breakaway development view of a sanitary napkin of an embodiment.
Figure 2:
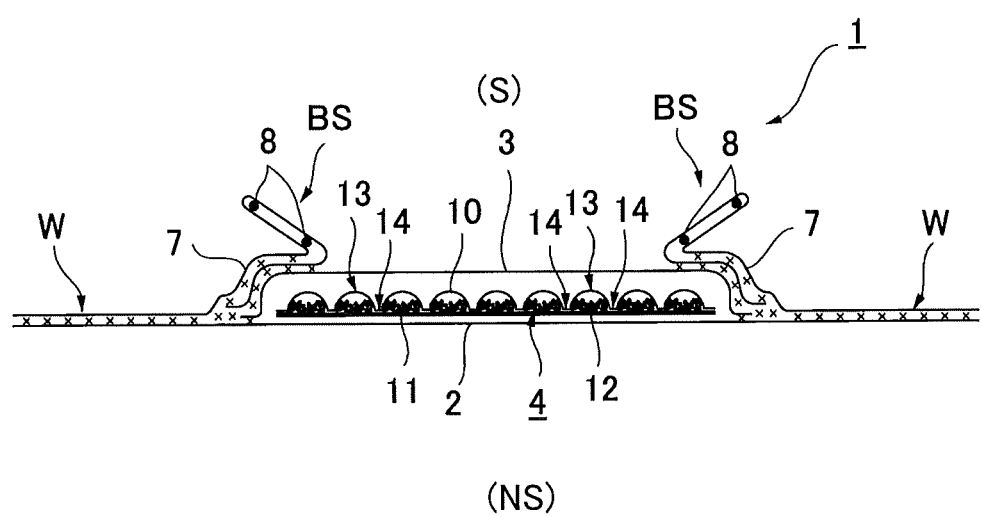
FIG. 2 is a cross-sectional view of FIG. 1 taken along a II-II line.

FIG. 1 is a partial breakaway development view of the sanitary napkin 1 of the embodiment. FIG. 2 is a cross-sectional view of FIG. 1 taken along a II-II line. In FIG. 1 and FIG. 2, a front side of the sanitary napkin 1 is expressed as (F), a rear side is expressed as (R), a longitudinal direction is expressed as "L", a width direction is expressed as "W", a skin side is expressed as (S) and a non-skin side is expressed as (NS).

As illustrated in FIG. 1 and FIG. 2, the sanitary napkin 1 of the embodiment includes a liquid impermeable backsheet 2 made of a polyethylene sheet, a polypropylene sheet and the like, a liquid permeable topsheet 3 that rapidly permeates menstrual blood, vaginal secretions and the like, a polymer sheet 4 provided between these sheets 2 and 3, and side non-woven-fabrics 7, 7 respectively provided at both side portions of a front surface along a longitudinal direction "L". The polymer sheet 4 includes two layer sheets (an upper layer sheet 10 and a lower layer sheet 11), and a superabsorbent polymer 12 provided therebetween. Around the polymer sheet 4 at front and rear end portions in a napkin-longitudinal direction "L", outer end portions of the liquid impermeable backsheet 2 and the liquid permeable topsheet 3 are bonded with an adhesive such as a hot-melt adhesive or adhesive means such as a heat seal. Further, at lateral end portions, the liquid impermeable backsheet 2 laterally protruding from the polymer sheet 4 and the side non-woven-fabrics 7 are bonded with an adhesive such as a hot-melt adhesive or adhesive means such as a heat seal, and a peripheral flap portion at which the polymer sheet 4 does not exist is formed at the peripheral.

Hereinafter, a structure of the sanitary napkin 1 is further described in detail.

As the liquid impermeable backsheet 2, a sheet material having at least a water shielding property such as an olefin series resin sheet such as polyethylene or polypropylene is used, and in addition to this, a laminated non-woven-fabric in which a non-woven-fabric is stacked on a polyethylene sheet and the like, or further, a non-woven fabric sheet and the like may be used after ensuring substantial impermeability by interposing a waterproof film (in this case, the liquid impermeable backsheet is composed of the waterproof film and the non-woven fabric sheet). In recent years, a material having moisture permeability is often preferably used to prevent sweating. As this waterproof and moisture permeable sheet material, a microporous sheet obtained by forming a sheet by melting and kneading inorganic filler in olefin series resin such as polyethylene or polypropylene and then extruding the sheet in one axial direction or two axial directions, is used.

As the liquid permeable topsheet 3, a perforated or imperforate non-woven fabric, a porous plastic sheet or the like is preferably used. For example, a regenerated fiber such as rayon or cupra (cuprammonium rayon), and a natural fiber such as cotton, may be used as a material fiber forming the non-woven fabric in addition to a synthetic fiber including an olefin series such as polyethylene or polypropylene, a polyester series, a polyamide series or the like. As the non-woven fabric, a non-woven fabric obtained by a proper processing method such as a spun lace method, a spun bond method, a thermal bond method, a melt blown method or a needle punch method may be used. Among these processing methods, the spun lace method is superior in terms of great flexibility, the spun bond method is superior in terms of drape properties, and the thermal bond method and an air-through method are superior in terms of bulkiness and high compression and restoration properties. Although either of a long fiber or a short fiber may be used as the non-woven-fabric, in order to provide texture of towel cloth, it is preferable to use the short fiber. Further, in order to facilitate an embossing process, an olefin series fiber such as polyethylene or polypropylene whose melting point is relatively low may be used. Furthermore, a composite fiber such as a core-clad type fiber including a core made of a fiber with a high melting point and a clad made of a fiber with a low melting point, a side-by-side type fiber, a division type or the like, may be also used. The liquid permeable topsheet 3 may not be provided when the upper layer sheet 10 of the polymer sheet 4, which will be described later in detail, constitutes a skin contacting surface layer.

The polymer sheet 4 provided between the liquid impermeable backsheet 2 and the liquid permeable topsheet 3 has a structure in which the superabsorbent polymer 12 is provided between the upper layer sheet 10 positioned at a skin side (a liquid permeable topsheet 3 side, (S) side) and the lower layer sheet 11 positioned at a non-skin side (a liquid impermeable backsheet 2 side, (NS) side). The superabsorbent polymer 12 is not mixed in a fiber absorbent material such as a pulp, and provided as an assembly of only the superabsorbent polymer 12 in a powder form. Thus, the polymer sheet 4 becomes thin to make the sanitary napkin 1 thin. The polymer sheet 4 is described later in detail.

The side non-woven-fabrics 7, 7 are provided at the front surface side of the sanitary napkin 1 of the embodiment at both side portions, respectively, along the longitudinal direction "L" and over substantially the entire length of the napkin 1. Parts of the side non-woven-fabrics 7, 7 are extended toward both sides to form wing flaps W, W with parts of the liquid impermeable backsheet 2 that are similarly extended toward both sides, respectively.

As the side non-woven-fabric 7, either water-repellent non-woven fabric or hydrophilic non-woven fabric may be used depending on the desired function. For example, when regarding a function of preventing menstrual blood, vaginal secretions and the like from permeating or of improving a texture as important, it is preferable to use a water-repellent non-woven fabric coated with a water-repellent agent and the like of a silicon series, a paraffin series and an alkyl chromic chloride series. When regarding the absorbability of the menstrual blood and the like as important, it is preferable to use a hydrophilic non-woven fabric obtained by making a swellable or porous synthetic fiber by a method of polymerizing the synthetic fiber in the presence of a compound having a hydrophilic group, for example, an oxidation product of polyethylene glycol, in the manufacture of the synthetic fiber, or a method of treating the surface with a metallic salt such as stannic chloride to partially dissolve the surface to form a porous surface and then to precipitate a metallic hydroxide on the surface, and then providing the hydrophilic property for the synthetic fiber using capillary action.

As illustrated in FIG. 2, an inner side of the side non-woven-fabric 7 is bent such that the side non-woven-fabric 7 is substantially doubly bent, one or a plurality of, two in the illustrated example, threadlike elastic stretchable members 8, 8 are provided in this double sheet at a middle portion in the height direction, where both ends or appropriate positions in the longitudinal direction "L" of each of the threadlike elastic stretchable members 8, 8 are fixed, and standing gathers BS, BS are formed by standing the double sheet portions toward the skin side by contraction force of the threadlike elastic stretchable members 8, 8.

(About Polymer Sheet 4)

Hereinafter, the polymer sheet 4 is described in detail. As the upper layer sheet 10 constituting the polymer sheet 4, a perforated or imperforate non-woven fabric or a porous plastic sheet is used. As a material fiber constituting the non-woven-fabric, similarly as the liquid permeable topsheet 3, for example, a regenerated fiber such as rayon or cupra (cuprammonium rayon), and a natural fiber such as cotton may be used in addition to a synthetic fiber including an olefin series such as polyethylene or polypropylene, a polyester series, a polyamide series or the like. Although a processing method of the non-woven-fabric is not limited, in order to prevent removal of the superabsorbent polymer 12, it is preferable to use a processing method by which a product with high fiber density is obtained such as a spun bond method, a melt blown method or a needle punch method. It is preferable that a diameter of a hole of the porous plastic sheet is smaller than an outer diameter of the superabsorbent polymer 12 in order to prevent removal of the superabsorbent polymer 12. Further, as will be described later in detail, as a predetermined unevenness process is performed on the upper layer sheet 10, it is preferable to include a material having a thermoplastic property.

As the lower layer sheet 11, in addition to the perforated or imperforate non-woven fabric or the porous plastic sheet, a sheet material having a water shielding property may be used. Similarly as the upper layer sheet 10, although a processing method of the non-woven-fabric is not limited, in order to prevent removal of the superabsorbent polymer 12, it is preferable to use a processing method by which a product with high fiber density is obtained such as a spun bond method, a melt blown method or a needle punch method. It is preferable that a diameter of a hole of the porous plastic sheet is smaller than an outer diameter of the superabsorbent polymer 12 in order to prevent removal of the superabsorbent polymer 12. As the sheet material having a water shielding property, a material same as the liquid impermeable backsheet 2 may be used.

As the superabsorbent polymer 12, a cross-linking polyacrylate, a self-cross-linking polyacrylate, a saponified substance of a cross-linking copolymer of acrylic acid ester and vinyl acetate, a cross-linking substance of a copolymer of isobutylene and maleic anhydride, a cross-linking polysulfonate, and a partially cross-linking substance of a water swellable polymer such as polyethylene oxide or polyacrylamide are exemplified. Among these examples, a substance of acryl acid or an acrylate-based substance having a large amount of water absorption and a high absorption speed is preferable. The water-absorbing power and the water absorption speed of the superabsorbent polymer having the above-mentioned water absorption performance can be adjusted by adjusting a cross-linking density and a cross-linking density gradient in its manufacturing process.

Figure 3:
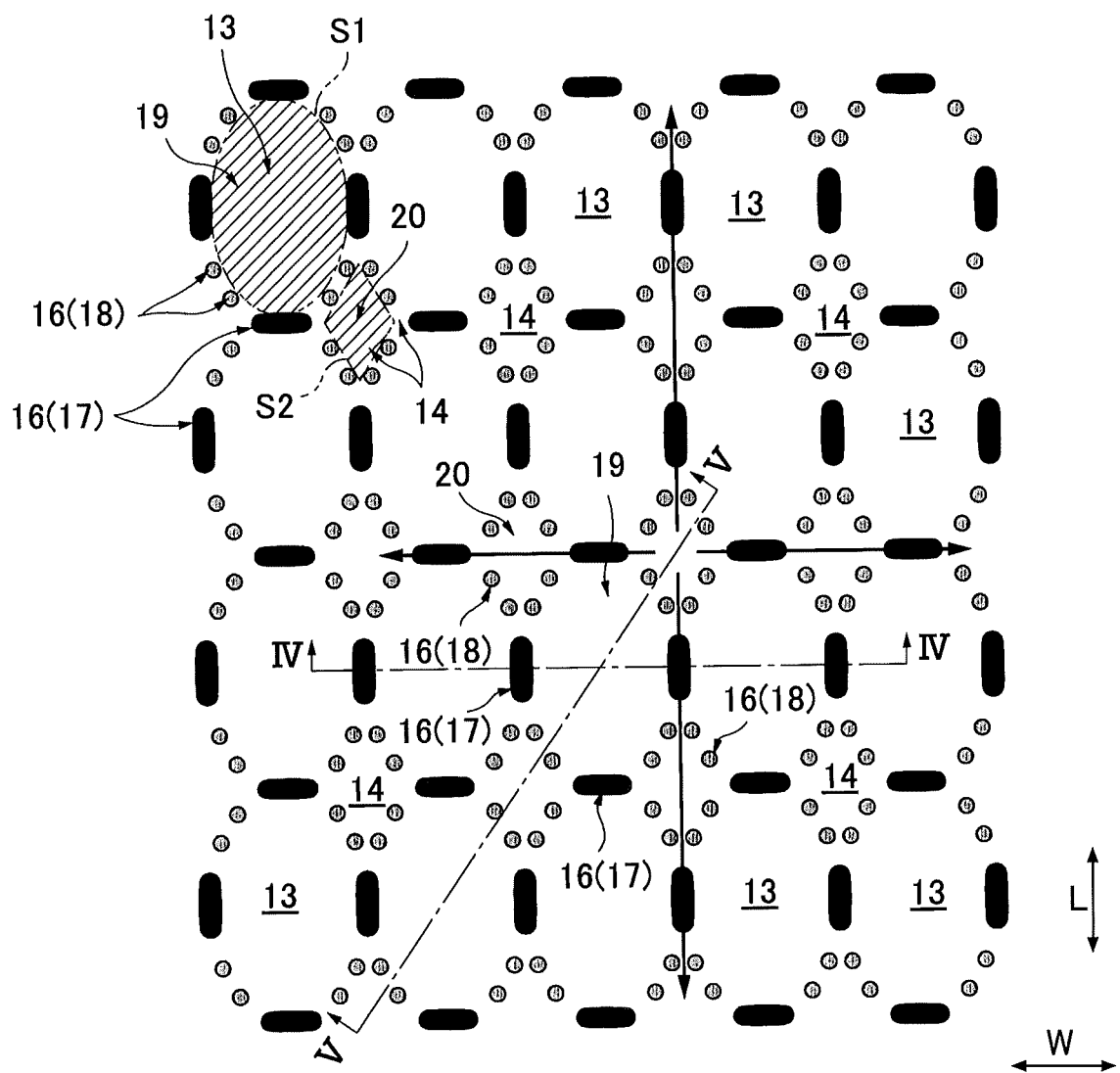
FIG. 3 is an enlarged plan view of a polymer sheet.

FIG. 3 is an enlarged plan view of the polymer sheet 4. As illustrated in FIG. 3, polymer provided regions 13 at each of which the superabsorbent polymer 12 is provided, and polymer non-provided regions 14 at each of which the superabsorbent polymer 12 is not provided are formed at the polymer sheet 4. The polymer provided region 13 is a region at which the superabsorbent polymer 12 greater than or equal to a predetermined fabric weight per unit area is provided between the upper layer sheet 10 and the lower layer sheet 11. The polymer non-provided region 14 is a region adjacent to the polymer provided regions 13 and other than the polymer provided regions 13, and is a region at which the superabsorbent polymer 12 is not provided between the two sheets 10 and 11 at all, or a region at which a slight amount of the superabsorbent polymer 12 exists due to falling of the superabsorbent polymer 12 when scattering the superabsorbent polymer 12 at the polymer provided regions 13 but the amount is extremely small compared with that at the polymer provided regions 13. The polymer provided regions 13 are formed at an area that does not reach an outer edges of the upper layer sheet 10 and the lower layer sheet 11.

Figure 4:
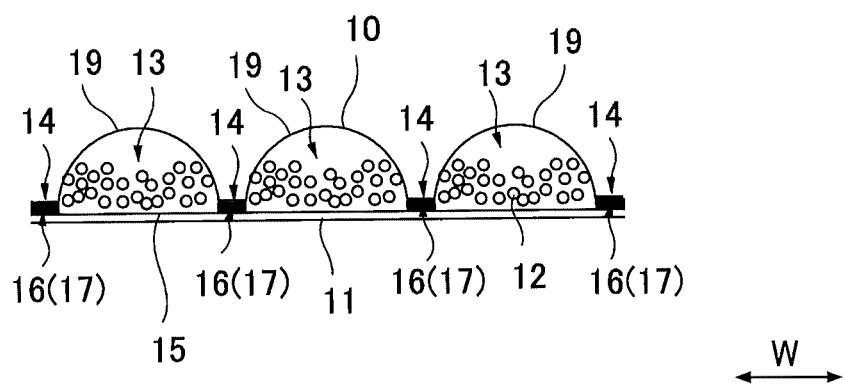
FIG. 4 is a cross-sectional view of FIG. 3 taken along a IV-IV line.
Figure 5:
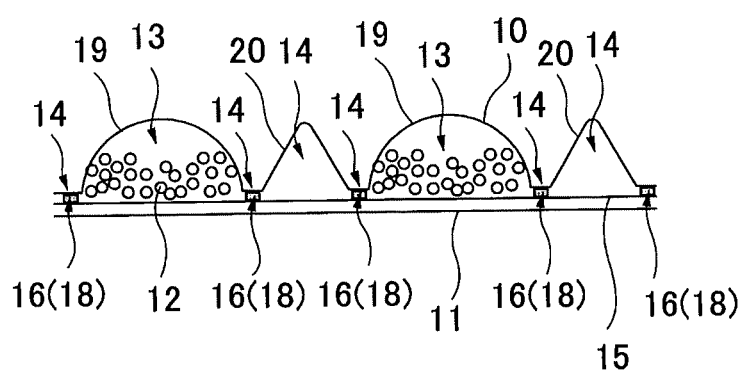
FIG. 5 is a cross-sectional view of FIG. 3 taken along a V-V line.

FIG. 4 is a cross-sectional view of FIG. 3 taken along a IV-IV line. FIG. 5 is a cross-sectional view of FIG. 3 taken along a V-V line. As illustrated in FIG. 4 and FIG. 5, the polymer sheet 4 includes a liquid diffusion sheet 15, adjacently stacked on the skin side surface (upper surface in the drawing) of the lower layer sheet 11, that promotes diffusion of the body fluid in a plane direction. In other words, the polymer sheet 4 has a structure in which the liquid diffusion sheet 15 is stacked on an upper surface of the lower layer sheet 11, the polymer provided regions 13 and the polymer non-provided regions 14 are formed at an upper surface of the liquid diffusion sheet 15, and the upper layer sheet 10 is further stacked on an upper surface of the regions.

It is preferable that the liquid diffusion sheet 15 is constituted by a fiber assembly having a good diffusion property for the body fluid in the plane direction, and also having liquid permeability in the thickness direction lower than that of the upper layer sheet 10 and the lower layer sheet 11. As a material having such properties, for example, a crepe paper or a tissue paper may be exemplified.

It is preferable that the liquid diffusion sheet 15 is only provided at the non-skin side of the superabsorbent polymer 12, and not provided at the skin side of the superabsorbent polymer 12. If the liquid diffusion sheet 15 is provided at the skin side of the superabsorbent polymer 12, there is a risk that absorbing speed of the polymer sheet 4 is lowered because a permeation rate of urine in the thickness direction is lowered by the liquid diffusion sheet 15.

The liquid diffusion sheet 15 may be constituted by a single layer, or may be constituted by a multi-layered structure in which plurality of sheets are stacked. When the liquid diffusion sheet 15 is constituted by the multi-layered structure, the multi-layered structure may be formed by stacking sheet members all having the same property, or may be formed by stacking sheet members having different properties. In other words, at least one layer is constituted to have a good diffusion property for the body fluid in the plane direction, and also have a low liquid diffusion property in the thickness direction, or at least one layer is constituted to have a good diffusion property for the body fluid in the plane direction, and at least another one layer is constituted to have low liquid permeability in the thickness direction. For the latter case, it is preferable to place such that a layer constituting the skin side surface (first sheet) has a good diffusion property for the body fluid in the plane direction, and a layer constituting the non-skin side surface (second sheet) has low liquid permeability in the thickness direction. In such a case, at least the layer constituting the skin side surface (first sheet) may have predetermined Klemm water absorbency, which will be described in the following.

As the good diffusion property for the body fluid in the plane direction that should be provided to the liquid diffusion sheet 15, it is preferable that Klemm water absorbency defined by "Determination of water absorptiveness of Paper and board by a Klemm method" of JIS P8141, by 10 minutes, is greater than or equal to 25 mm, in particular, greater than or equal to 30 mm. As a material having such a property, specifically, a thin absorbent paper such as a crepe paper or a tissue paper is preferable.

Specifically, results of measuring Klemm water absorbency for following each material are illustrated in Table 1. The measurement was measured ten times in each of a line direction of the respective material (MD) and a direction perpendicular to that direction (CD), and each average value was used as the Klemm water absorbency. The materials used for the measurement were three types including (1) the liquid diffusion sheet 15 (crepe paper, 15 g/m$^2$), (2) an air-through non-woven-fabric (a stacked layer of a composite fiber of polyethylene/polypropylene, and a composite fiber of polyethylene/polyethylene terephthalate, 25 g/m$^2$), and (3) a spun bond non-woven-fabric (polypropylene, 18 g/m$^2$). As illustrated in Table 1, although the Klemm water absorbency is largely different depending on the material, the material of (1) used in this embodiment has a good liquid diffusion property in the plane direction.

TABLE 1

| MATERIAL | MD | CD |
| --- | --- | --- |
| (1) | 27.3 mm | 27.6 mm |
| (2) | 1.3 mm | 4.4 mm |
| (3) | 0.0 mm | 0.8 mm |

It is preferable that liquid permeability of the liquid diffusion sheet 15 in the thickness direction is lower than that of the upper layer sheet 10 and the lower layer sheet 11. It is preferable to have such a property because the body fluid absorbed in the liquid diffusion sheet 15 does not immediately move to the lower layer sheet 11, but the body fluid diffuses in the liquid diffusion sheet 15 over a wider range, and can contact a greater amount of the superabsorbent polymer 12. With this, the superabsorbent polymer 12 can more surely absorb the body fluid.

As a material having such a property, a thin absorbent paper such as a crepe paper or a tissue paper, a fiber assembly such as a non-woven-fabric whose hydrophilic degree is lower than that of the upper layer sheet 10 and the lower layer sheet 11, a perforated film and the like may be used.

As illustrated in FIG. 1, it is preferable that the liquid diffusion sheet 15 is formed to have substantially the same shape as that of the upper layer sheet 10 and the lower layer sheet 11, or formed to be slightly smaller than them but at least has a size that can cover all of the polymer provided regions 13. Further, the liquid diffusion sheet 15 may be provided only at a portion at which the diffusion of the body fluid in the plane direction is to be promoted, for example, at a urine expelling port corresponding region and its surrounding region.

At the polymer non-provided regions 14, the upper layer sheet 10 is bonded by predetermined bonded portions 16 under a state that the upper layer sheet 10 directly contacts the liquid diffusion sheet 15. For the bonded portions 16, adhesive means such as a hot-melt adhesive or welding means by heat or ultrasonic waves may be used. It is preferable to provide the bonded portions 16 in a pattern surrounding each of the polymer provided regions 13.

At the polymer non-provided regions 14, the upper layer sheet 10 is provided such that at least portions where the bonded portions 16 are formed are directly contacting the liquid diffusion sheet 15. Portions other than the bonded portions 16 may not contact the liquid diffusion sheet 15, a part of the portions may contact the liquid diffusion sheet 15 and another part of the rest of the portions may not directly contact the liquid diffusion sheet 15 by protruding toward the skin side than the liquid diffusion sheet 15 and the like, or all of the upper layer sheet 10 at the polymer non-provided regions 14 may directly contact the liquid diffusion sheet 15.

The bonded portion 16 is formed by bonding at least the upper layer sheet 10 and the liquid diffusion sheet 15, and further, it is preferable to integrally bonding also with the lower layer sheet 11. The lower layer sheet 11 may be bonded with the upper layer sheet 10 or the liquid diffusion sheet 15 at least at a peripheral portion. However, it is preferable to bond the lower layer sheet 11 with the liquid diffusion sheet 15 and the upper layer sheet 10 at the bonded portions 16 from a viewpoint of increasing the bonding strength of the bonded portions 16.

According to the polymer sheet 4 having the above described structure, as the upper layer sheet 10 is bonded with the liquid diffusion sheet 15 under a state that the upper layer sheet 10 directly contacts the liquid diffusion sheet 15 at the polymer non-provided regions 14, at the polymer non-provided regions 14, urine permeated from the upper layer sheet 10 to the liquid diffusion sheet 15 can rapidly diffuse in the plane direction by a liquid diffusion action of the liquid diffusion sheet 15 in the plane direction, the urine contacts the superabsorbent polymer 12 over a wide range, and the urine can be efficiently absorbed. Further, as the urine diffused in the plane direction by the liquid diffusion sheet 15 is absorbed from a lower side of the superabsorbent polymer 12 provided in the polymer provided regions 13, the superabsorbent polymer 12 can efficiently absorb the body fluid. Further, as the urine diffused in the plane direction by the liquid diffusion sheet 15 is absorbed by the superabsorbent polymer 12 over the wide region, worsening of fit by increasing in thickness due to swelling of the superabsorbent polymer 12 at a specific narrow region as the body fluid is locally absorbed only by the superabsorbent polymer 12 at the specific narrow region can be prevented.

As illustrated in FIG. 3, it is preferable that the polymer sheet 4 has a structure, in planar view, that is sectioned into a plurality of first defined regions 19, 19 . . . , and second defined regions 20 each of which is positioned at a center of the four adjacent first defined regions 19, 19 . . . , and each of whose inside is configured as the polymer non-provided region 14. Each of the first defined regions 19 is surrounded by the bonded portions 16 that bonds the upper layer sheet 10 with the liquid diffusion sheet 15 at least at upper, lower, left and right directions. The plurality of first defined regions 19, 19 . . . may be aligned in a square lattice form along the longitudinal direction "L" and in the width direction "W" of the sanitary napkin 1, and may be constituted that their insides are the polymer provided regions 13.

When describing more specifically, as illustrated in FIG. 3, in the polymer sheet 4, the upper layer sheet 10 and the liquid diffusion sheet 15 are bonded by first bonded portions 17 that are provided to align in a zigzag form, and also bonded by second bonded portions 18 that are provided at oblique intermediate positions connecting each two of the four first bonded portions 17, 17 . . . that are provided at upper, lower, left and right positions. The zigzag form means the first bonded portions 17 are aligned such that that adjacent rows or columns having the same pitch are alternately shifted for a half pitch, and alternately aligned in the vertical direction or in the lateral direction. Further, in this document, upper and lower positions mean positions in a direction that match the longitudinal direction "L" (front and rear direction) of the sanitary napkin 1, left and right positions mean positions in a direction that matches the width direction "W" of the sanitary napkin 1.

The polymer sheet 4 is sectioned into the plurality of first defined regions 19 each surrounded by the first bonded portions 17 and the second bonded portions 18, aligned in a square lattice form along the napkin-longitudinal direction "L" and in the width direction W, and in each of which the superabsorbent polymer 12 is sealed, and the second defined regions 20 each positioned at a center of the four adjacent (adjacent in a vertical direction and in a lateral direction) first defined regions 19, 19 . . . , and, surrounded by the second bonded portions 18 at four oblique directions, respectively.

In other words, each of the first defined regions 19 is surrounded by the first bonded portions 17, 17 . . . that are positioned at upper, lower, left and right positions, respectively, and the second bonded portions 18, 18 . . . that are positioned at the four oblique positions each at the middle of two of the upper, lower, left and right positions. Each of the second defined regions 20 is positioned at a center of a region surrounded by the four first defined regions 19, 19 . . . aligned in a square lattice form, that are adjacent in the vertical direction and in the lateral direction, and is surrounded by the second bonded portions 18 at the four oblique directions.

When taking one of the first defined regions 19 as a reference, at a periphery, the other first defined regions 19 are adjacent at both end portions in the pad-longitudinal direction "L", respectively, the other first defined regions 19 are adjacent at both side portions in the pad-width direction "W", respectively, and the second defined regions 20 are adjacent at the four oblique directions, which are also the middle of each two of the first defined regions 19, 19 . . . provided around the reference first defined region 19.

As illustrated in FIG. 3 and FIG. 4, at the first defined region 19, the upper layer sheet 10 at a region surrounded by the first bonded portions 17 and the second bonded portions 18 bulges toward the skin side like a dome having an approximately center portion as an apex. With this, a space portion is formed between the upper layer sheet 10 and the liquid diffusion sheet 15. As illustrated in FIG. 3 and FIG. 5, in the second defined region 20, the upper layer sheet 10 at a region whose four oblique directions are surrounded by the second bonded portions 18 bulges toward the skin side in a pyramid-like shape substantially having an approximately center portion as an apex. With this, a space portion is formed between the upper layer sheet 10 and the liquid diffusion sheet 15.

Figure 6:
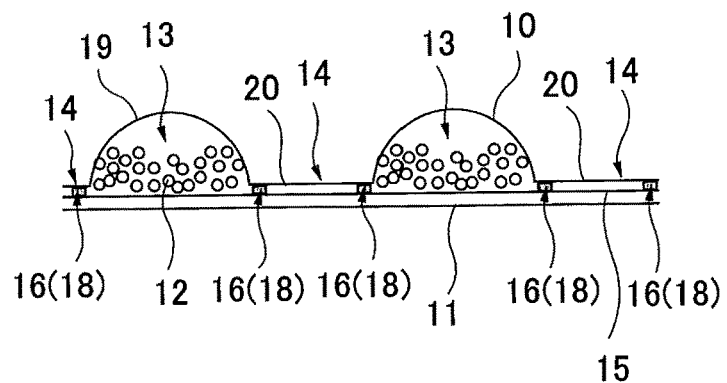
FIG. 6 is a cross-sectional view of FIG. 3 taken along the V-V line, of a modified example.

FIG. 6 is a cross-sectional view taken along a V-V line of FIG. 3 of a modified example. As illustrated in FIG. 6, by stacking a flat portion of the upper layer sheet 10 on the upper surface of the liquid diffusion sheet 15, it is possible not to form space portions between the upper layer sheet 10 and the liquid diffusion sheet 15. The first defined region 19 is formed to be the polymer provided region 13 at which the superabsorbent polymer 12 is filled in the inner space.

It is preferable that the bonding strength of the second bonded portion 18 is set to be smaller than the bonding strength of the first bonded portion 17 so that the second bonded portions 18 are preferentially peeled compared with the first bonded portions 17 when the superabsorbent polymer 12 is swelled by absorbing liquid. In other words, it is preferable to have a relationship that the bonding strength of the first bonded portion 17>the bonding strength of the second bonded portion 18. By setting the bonding strength of the second bonded portion 18 to be smaller than the bonding strength of the first bonded portion 17, when the superabsorbent polymer 12 is swelled by absorbing liquid, the second bonded portions 18 are peeled by relatively small force. Further, when the superabsorbent polymer 12 is further swelled and larger force is generated, the first bonded portions 17 are also peeled.

Figure 7:
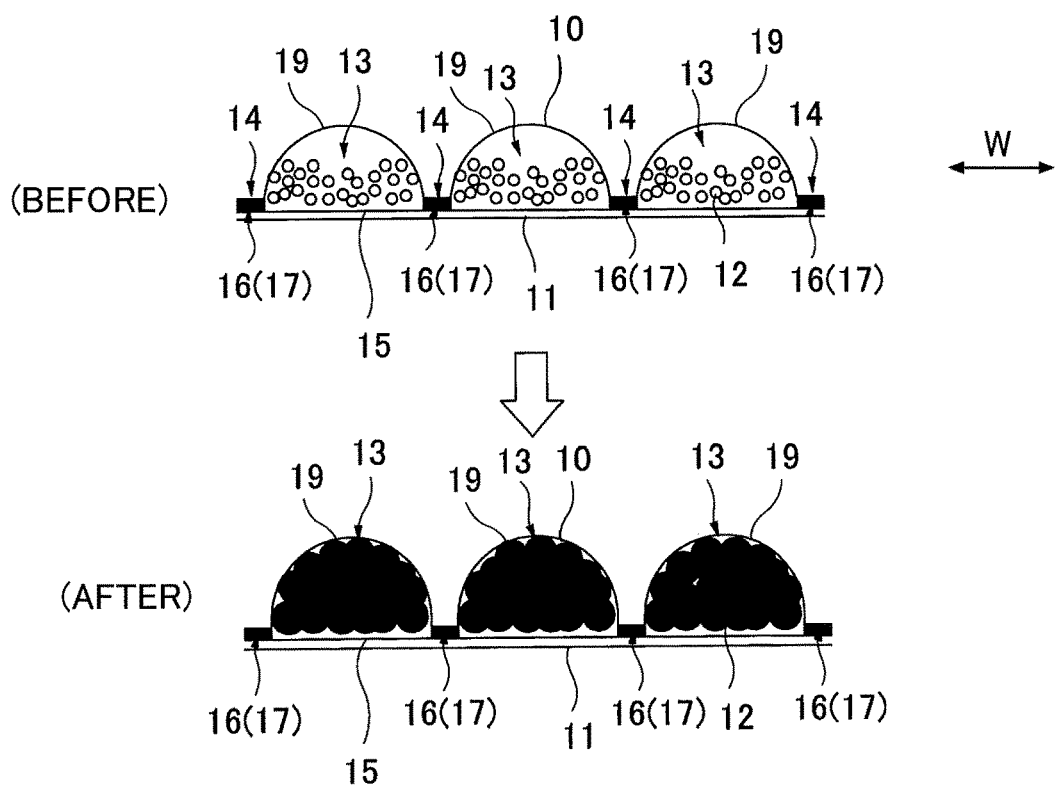
FIG. 7 is a cross-sectional view of FIG. 3 taken along the IV-IV line before and after absorbing water.

A body fluid absorption mechanism of the polymer sheet 4 having the above described structure is described with reference to FIG. 3, FIG. 7 and FIG. 8. First, as illustrated in FIG. 3 and FIG. 7, in a cross sectional view taken along a cross-section that passes through the first defined region 19 in the width direction "W" and passes through the first bonded portions 17, 17 at both sides of the defined region 19, at a portion between the first defined regions 19, 19 that are adjacent in the width direction "W", the upper layer sheet 10 and the liquid diffusion sheet 15 are bonded by the first bonded portion 17 having the relatively large bonding strength (before absorbing liquid, it is illustrated as (BEFORE) in the drawing). Thus, when the superabsorbent polymer 12 sealed in the first defined region 19 is swelled by absorbing liquid (after absorbing liquid, illustrated as (AFTER) in the drawing), the first bonded portion 17 is not easily peeled, and distortion or unevenness is easily formed at the upper layer sheet 10 or the liquid diffusion sheet 15 by the swelled superabsorbent polymer 12.

Figure 8:
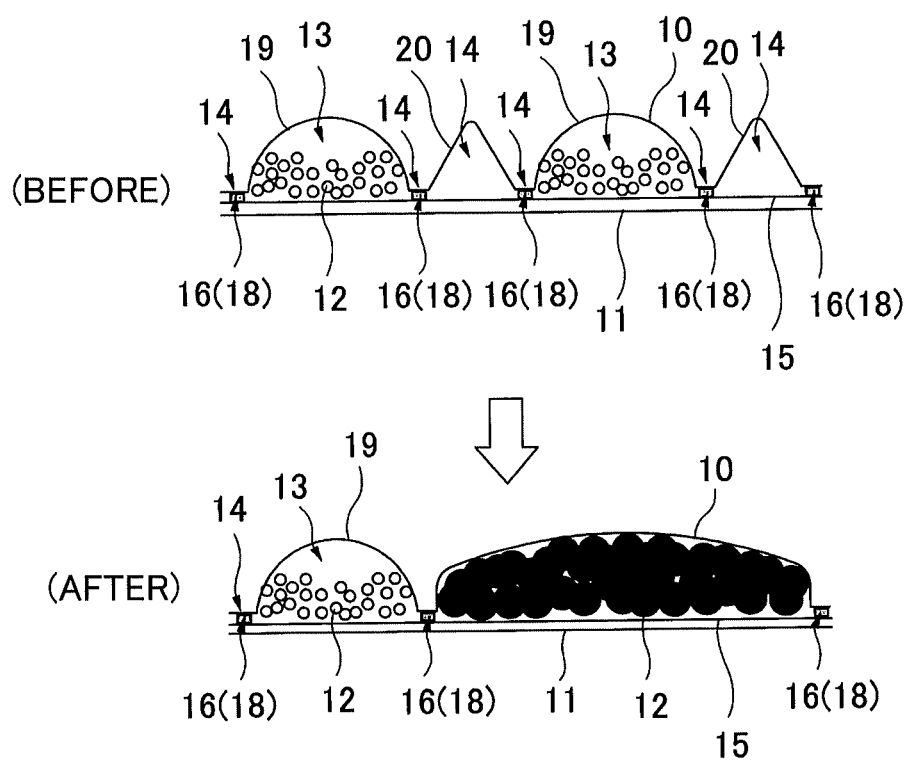
FIG. 8 is a cross-sectional view of FIG. 3 taken along the V-V line before and after absorbing water.

However, as illustrated in FIG. 3 and FIG. 8, according to the polymer sheet 4 of the embodiment, in a cross-sectional view taken along a cross-section that obliquely passes through the first defined region 19 and alternately passes through the first defined region 19 and the second defined region 20, at a portion between the first defined region 19 and the second defined region 20 that are adjacent in the oblique direction, the upper layer sheet 10 and the liquid diffusion sheet 15 are bonded by the second bonded portion 18 having the relatively small bonding strength (before absorbing liquid, illustrated as (BEFORE) in the drawing). Thus, when the superabsorbent polymer 12 sealed in the first defined region 19 is swelled by absorbing liquid (after absorbing liquid, illustrated as (AFTER) in the drawing), the second bonded portion 18 is peeled and the first defined region 19 and the second defined region 20 communicate with each other. Thus, a diffusion property of the body fluid becomes good, the superabsorbent polymer 12 swelled by absorbing liquid can flow easily, the superabsorbent polymer 12 does not easily bond with each other so that gel blocking does not occur, and the liquid can be efficiently absorbed by the superabsorbent polymer 12. Further, when the superabsorbent polymer 12 is swelled by absorbing liquid, as the inner space of the first defined region 19 communicates with the inner spaces of the second defined regions 20 in the four oblique directions, stress generated by swelling of the superabsorbent polymer 12 can be released, distortion or unevenness does not easily generated in the sheet, and fit becomes good. Further, in the polymer sheet 4, not all of the bonded portions around the first defined region 19 are peeled at the same time, but there are portions having weak bonding strength and portions having strong bonding strength, and the portions having weak bonding strength are preferentially peeled but the portions having strong bonding strength are left. With this, deformation or bias of the sheet due to a large movement of the polymer after swelling can be prevented.

As illustrated in FIG. 3, it is preferable to form the second defined region 20 to have a smaller area than that of the first defined region 19. With this, the second defined region 20 easily functions as a buffer zone to release stress generated when the polymer in the first defined region 19 is swelled without lowering a water absorbing efficiency of the polymer sheet, 4. Further, it is preferable that the inner space of the second defined region 20 to have a volume smaller than that of the first defined region 19. With this, when the inner spaces of the first defined region 19 and the second defined region 20 communicate with each other, distortion of the polymer sheet due to a large movement of the superabsorbent polymer 12 is prevented.

Each of the first defined region 19 and the second defined region 20 may be formed to have any planar shapes. The planar shape of the first defined region 19 means, as illustrated in FIG. 3, a planar shape of a base end portion of a region surrounded by the first bonded portions 17 and the second bonded portions 18, and means a planar shape of a closed virtual line "S1" that inscribes the first bonded portions 17 and the second bonded portions 18. The planar shape of the second defined region 20 means, as illustrated in FIG. 3, a planar shape of a base end portion surrounded by the second bonded portions 18, and a planar shape of a closed virtual line "S2" that inscribes the second bonded portions 18. The planar shape of the first defined region 19 may be an ellipse shape, a circular shape, a polygonal shape, a diamond shape and the like. The planar shape of the second defined region 20 may be a substantially diamond shape, an ellipse shape, a circular shape, a polygonal shape and the like. For a planar shape having a longitudinal direction and a short direction, the longitudinal direction may be aligned in the napkin-longitudinal direction "L", or may be aligned in the napkin-width direction "W". Among these planar shapes, as illustrated in FIG. 3, it is particularly preferable that the planar shape of the first defined region 19 is an ellipse shape that is longer in the napkin-longitudinal direction "L", and the planar shape of the second defined region 20 is a substantially diamond shape. With this, the first defined regions 19 and the second defined regions 20 are provided in the polymer sheet 4 with almost no spaces. Thus, the water absorbing efficiency of the polymer sheet 4 can be increased, and distortion of the sheet can be suppressed to be small when the superabsorbent polymer 12 is swelled by absorbing liquid, and the second bonded portions 18 are peeled so that the first defined regions 19 and the second defined regions 20 communicate with each other. The substantially diamond shape of the planar shape of the second defined region 20 includes a substantially diamond shape each of whose side is a curve protruding inside, in addition to a diamond shape each of whose side is a linear line.

As illustrated in FIG. 3, it is preferable that each of the first defined regions 19 and each of the second defined regions 20 are provided to be close to the adjacent first defined regions 19 or the second defined regions 20 without having spaces therebetween while having the first bonded portions 17 and the second bonded portions 18 as boundaries. With this, the superabsorbent polymer 12 can be provided in the polymer sheet 4 substantially including no spaces, and an absorption effect of liquid can be increased. Alternatively, each of the first defined regions 19 may be surrounded by the separately and independently provided first bonded portions 17 and second bonded portions 18 and may be provided to have spaces with the adjacent first defined regions 19, respectively (not illustrated). In such a case, when the superabsorbent polymer 12 in the first defined region 19 is swelled and the polymer sheet 4 becomes thick, a space between the adjacent first defined regions 19, 19 functions as a buffer zone to absorb distortion of the sheet, and distortion of the entire polymer sheet 4 can be prevented. When this space is too small, distortion of the sheet cannot be absorbed, but if this space is too large, an absorption effect of liquid is lowered. Thus, it is preferable that the space is approximately 10% to 30% of a length of the first defined region 19 in the longitudinal axial direction.

It is preferable that the inner space between the upper layer sheet 10 and the liquid diffusion sheet 15 in the first defined region 19 has a bottom surface having an ellipse shape that is longer in the napkin-longitudinal direction "L", in a cross-sectional view, is formed in a hollow arc shape that bulges toward the skin side from the surface of the liquid diffusion sheet 15 like a dome having entirely a round shape, and three-dimensionally, is formed as substantially semiellipsoid that is substantially cut ellipsoid in half along the longitudinal direction.

An inner space may be formed between the upper layer sheet 10 and the liquid diffusion sheet 15 in the second defined region 20 (see FIG. 5). In such a case, it is preferable that the inner space has a substantially diamond shaped bottom surface, in a cross-sectional view, is formed in a hollow triangle shape having linear inclined surface that is inclined toward the skin side from the surface of the liquid diffusion sheet 15, and three-dimensionally, is formed as a substantially pyramid-like shape. An angle of an apex portion of the inner space of the second defined region 20 may be formed as an acute angle, preferably, less than or equal to 60°, more preferably less than or equal to 45°.

When the second defined region 20 bulges, it is preferable that the bulging height of the first defined region 19 and the bulging height of the second defined region 20 are substantially the same. With this, the body fluid is easily transferred toward the absorbent body side in the second defined regions 20 while retaining good fit at the first defined regions 19. If the height of the second defined region 20 is higher than the height of the first defined region 19, apex portions of the second defined region 20 mainly contact the skin, and the feeling is worsened. It is desirable that a difference in heights of the first defined region 19 and the second defined region 20 is almost zero, but it is allowable to have a difference approximately ±3 mm, preferably approximately ±2 mm, and more preferably approximately ±1 mm.

However, in this embodiment, as illustrated in FIG. 6, the second defined region 20 may be formed to be flat where a space is not formed between the upper layer sheet 10 and the liquid diffusion sheet 15 (the structure illustrated in FIG. 6, for example). In such a case as well, as described above with reference to FIG. 7 and FIG. 8, when the superabsorbent polymer 12 is swelled by absorbing liquid, the bonding of the second bonded portion 18 can be peeled and the first defined regions 19 and the second defined regions 20 can communicate with each other. With this, stress due to the swelling of the superabsorbent polymer 12 can be released, distortion or unevenness is not easily generated, and fit becomes good.

For the first bonded portion 17 and the second bonded portion 18, it is preferable to use adhesive means by an adhesive such as a hot-melt adhesive, but bonding means by welding such as a heat seal or ultrasonic waves may also be used.

When the adhesive means by an adhesive is used, the bonding strengths of the first bonded portion 17 and the second bonded portion 18 may be adjusted by adjusting a coating amount per unit area, or a length of a coating pattern. When the bonding means by welding is used, the bonding strengths of the first bonded portion 17 and the second bonded portion 18 may be adjusted by adjusting a welding area or welding temperature.

Both of the bonding strength of the first bonded portion 17 and the bonding strength of the of the second bonded portion 18 are set to be strength at which the upper layer sheet 10 and the liquid diffusion sheet 15 are not torn when the superabsorbent polymer 12 is swelled by absorbing liquid, in other words, strength that is smaller than tensile strength of the upper layer sheet 10 and the liquid diffusion sheet 15. Specifically, it is preferable that the bonding strength of the first bonded portion 17 is approximately 0.5 to 2 N/25 mm, and it is preferable that the bonding strength of the second bonded portion 18 is approximately 0.2 to 1 N/25 mm. Further, it is preferable that a difference in these bonding strengths is greater than or equal to 0.3 N/25 mm.

The bonding strength may be measured by tensile strength obtained by conducting a tension test in which a sheet material cut to have a width of 25 mm and bonded by each bonded portion is pulled at speed of 300 mm/min. Further, bonding strength of each of the bonded portions 17 and 18 may be measured by a following method by using a sheet at which the first bonded portion 17 and the second bonded portion 18 are actually provided. First, under a state that the upper layer sheet 10 and the liquid diffusion sheet 15 are bonded by the first bonded portion 17 and the second bonded portion 18, a tension test is conducted to measure bonding strength "P1". Next, under a state that the upper layer sheet 10 and the liquid diffusion sheet 15 are bonded only by the first bonded portion 17 by pouring water to the polymer sheet to swell the superabsorbent polymer 12 and peel (separate) the second bonded portion 18, the tension test is conducted to measure bonding strength "P2" (the bonding strength "P2" at this time is used as the bonding strength of the first bonded portion 17.). A difference between the bonding strengths "P1" and "P2" (P1-P2) is used as the bonding strength of the second bonded portion 18.

As illustrated in FIG. 3, it is preferable that the first bonded portions 17 respectively provided at upper and lower ends of the first defined region 19 are formed as grooves that are longer in the lateral direction (napkin-width direction "W"), and it is preferable that the first bonded portions 17 respectively provided at left and right ends of the first defined region 19 are formed as grooves that are longer in the vertical direction (napkin-longitudinal direction "L"). With this, each of the first bonded portions 17, provided between the adjacent first defined regions 19, 19 is formed as a groove that is longer in a direction of tangent lines connected with each other to limit connection between the adjacent first defined regions 19. Here, it is preferable that the first bonded portion 17 is formed as a continuous groove, but may be formed as intermittent dots.

Further, it is preferable that the second bonded portions 18 are placed to be apart from the first bonded portions 17, and formed in a plurality of dots that are intermittently provided in a direction connecting the adjacent first bonded portions 17, 17. It is preferable that the second bonded portions 18 are formed as intermittent dots whose bonding strength becomes weaker than that of the first bonded portion 17 so that the second bonded portions 18 are preferentially peeled when the superabsorbent polymer 12 is swelled by absorbing liquid. Further, the second bonded portion 18 may be formed as a continuous groove, or may be formed by a single dot. For example, the planar size of each of the second bonded portions 18 may be formed to be smaller than the planar size of each of the first bonded portions 17.

The second defined region 20 is formed as the polymer provided region 13 in which an amount of the superabsorbent polymer 12 less than that in the first defined region 19 is sealed, or formed as the polymer non-provided region 14 in which the superabsorbent polymer 12 is not provided. As the second defined region 20 is formed to have an area smaller than that of the first defined region 19, and its inner space has a volume smaller than that of the first defined region 19, it is preferable that a sealing amount of the superabsorbent polymer 12 is relatively small. Further, by forming the second defined region 20 to include an amount of the polymer less than that of the first defined region 19, or to be the polymer non-provided region 14, the superabsorbent polymer 12, that absorbs liquid and swells when the bonded portions between the first defined region 19 and the second defined region 20 are peeled (separated), can easily flow from the first defined region 19 to the second defined region 20, and gel blocking at the first defined region 19 can be more surely prevented.

Here, he weight of the superabsorbent polymer 12 filled in the first defined region 19 may be 20 to 300 g/m$^2$, preferably, 80 to 200 g/m$^2$.

Figure 9:
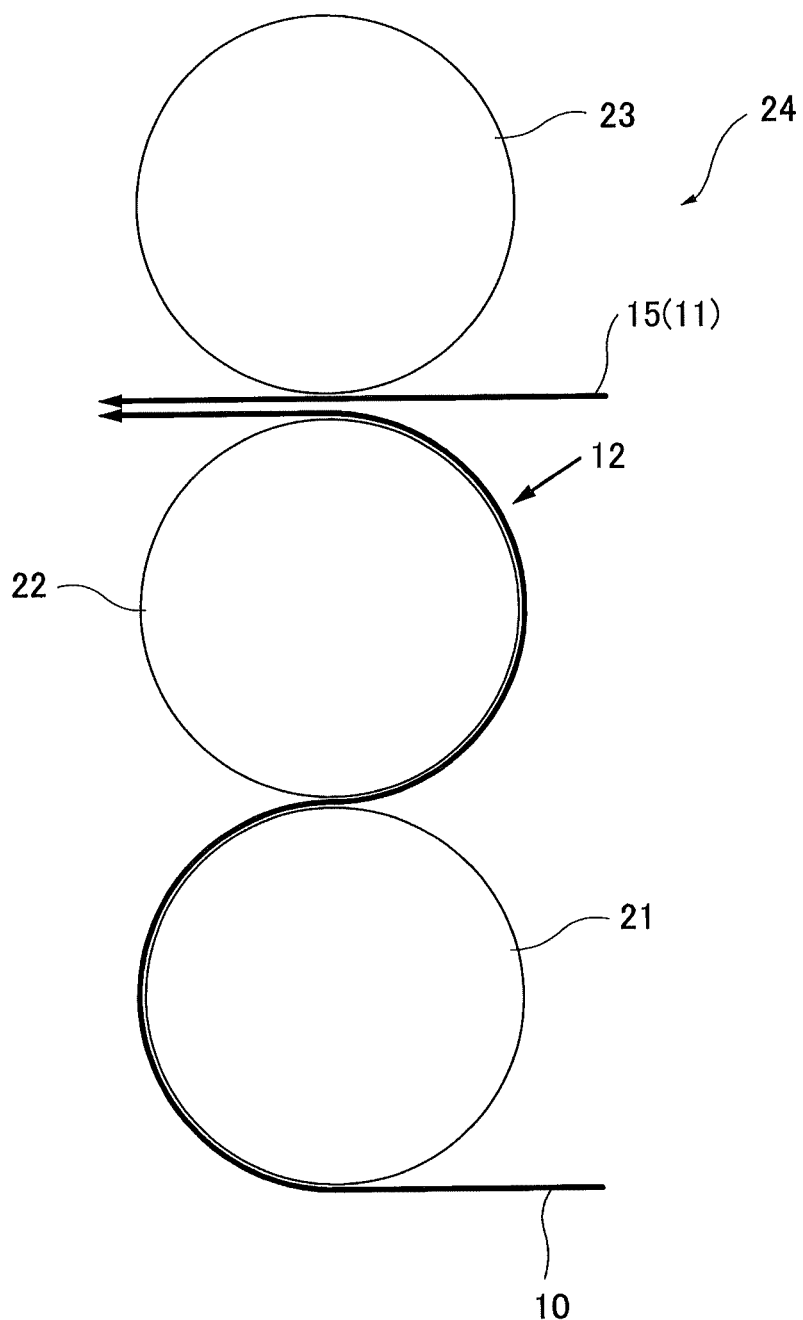
FIG. 9 is a side view illustrating a manufacturing device of a polymer sheet.
Figure 10:
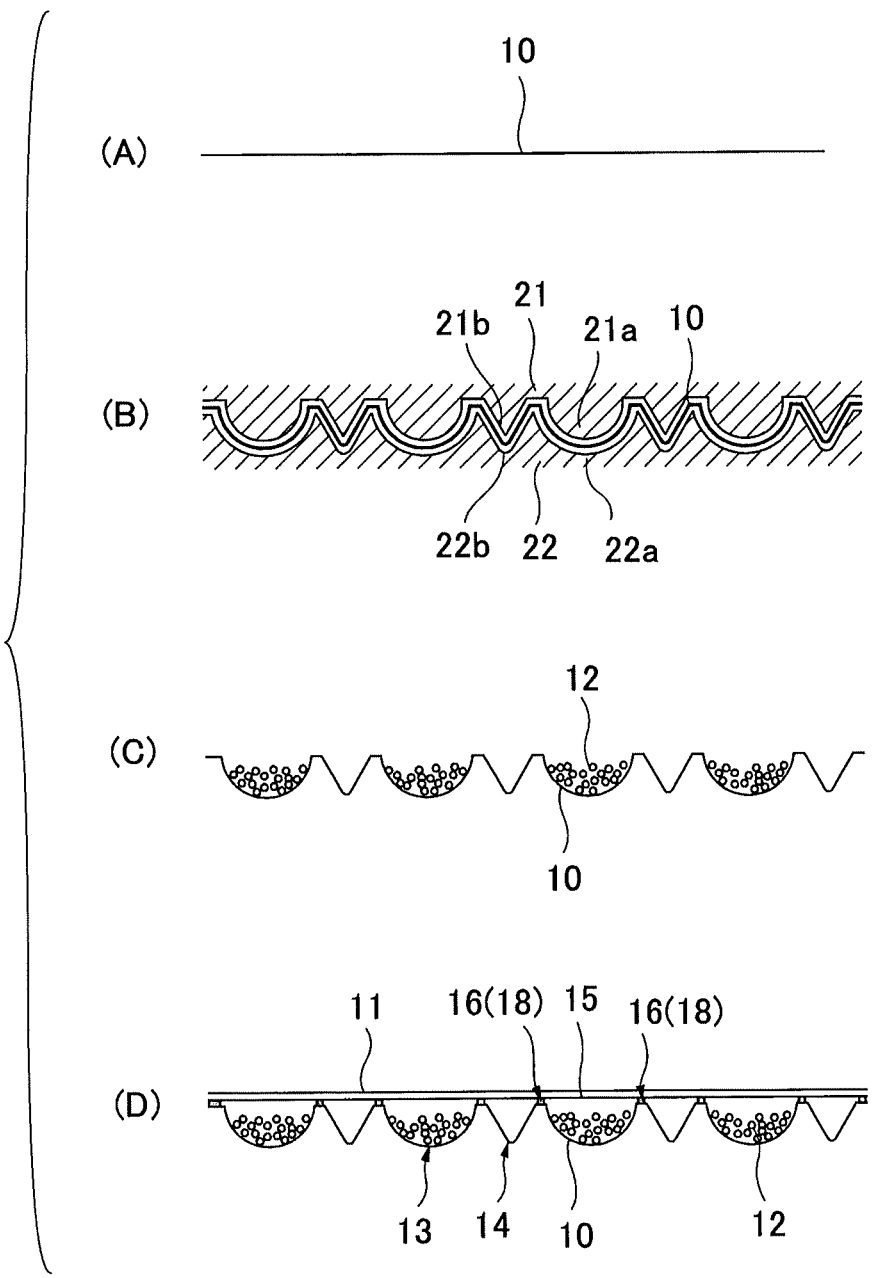
FIG. 10 is a cross-sectional view illustrating a manufacturing steps of the polymer sheet.

Next, manufacturing steps of the polymer sheet 4 are described with reference to FIG. 9 and FIG. 10. FIG. 9 is a side view illustrating a manufacturing device 24 of a polymer sheet. FIG. 10 is a cross-sectional view illustrating the manufacturing steps of the polymer sheet 4.

It is preferable to use the manufacturing device 24 for manufacturing the polymer sheet 4. The manufacturing device 24 includes a first emboss roller 21, a second emboss roller 22 and a flat roller 23. As illustrated in FIG. 10-(B), a plurality of protrusion portions 21a, 21a . . . corresponding to the first defined regions 19, and a plurality of protrusion portions 21b, 21b . . . corresponding to the second defined regions 20 are aligned on the first emboss roller 21. Further, a plurality of concave portions 22a, 22a . . . corresponding to the protrusion portions 21a of the first emboss roller 21, and a plurality of concave portions 22b, 22b . . . corresponding to the protrusion portions 21b of the first emboss roller 21 are aligned on the second emboss roller 22.

When manufacturing the polymer sheet 4, first, the upper layer sheet 10 (FIG. 10-(A)) is passed through between the first emboss roller 21 and the second emboss roller 22. With this, by an engagement of the protrusion portions 21a and the concave portions 22a, respectively, the bulging portions of the first defined regions 19 are formed, and also, by an engagement of the protrusion portions 21b and the concave portions 22b, respectively, the bulging portions of the second defined regions 20 are formed (FIG. 10-(B)).

Thereafter, by scattering the superabsorbent polymer 12 at a surface of the second emboss roller 22 on which the upper layer sheet 10 is placed, the superabsorbent polymer 12 is reserved in the concave portions 22a corresponding to the first defined regions 19 (FIG. 10-(C)).

Subsequently, by passing the liquid diffusion sheet 15, transferred from another path, between the second emboss roller 22 and the flat roller 23 to stack, the upper layer sheet 10 and the liquid diffusion sheet 15 are bonded and integrated by the first bonded portions 17 and the second bonded portions 18 (FIG. 10-(D)). Such a bonding may be performed by, coating a hot-melt adhesive and the like at an outer surface of the upper layer sheet 10 corresponding to the protrusion portions of the second emboss roller 22 and bonding with the liquid diffusion sheet 15, or by heating the protrusion portions of the second emboss roller 22 or by irradiating ultrasonic waves when engaging with the flat roller 23 and welding the upper layer sheet 10 and the liquid diffusion sheet 15. Further, at this time, by stacking the lower layer sheet 11 on the liquid diffusion sheet 15, in accordance with necessity, the upper layer sheet 10, the liquid diffusion sheet 15 and the lower layer sheet 11 are integrally bonded.

By providing an aspiration port at a bottom portion of the concave portion 22a, and in accordance with necessity, at a bottom portion of the concave portion 22b of the second emboss roller 22, the upper layer sheet 10 may be aspirated when embossing to facilitate embossing, and also when scattering the superabsorbent polymer 12 to prevent falling of the polymer. Further, after scattering the superabsorbent polymer 12, the amount of the superabsorbent polymer 12 included in each of the first defined regions 19 may be adjusted by smoothing a surface by a scraper and the like.

Thereafter, the polymer sheet 4, 4 . . . continuously provided in the longitudinal direction "L" is cut at the bonded portions of the upper layer sheet 10 and the lower layer sheet 11 at which the first defined regions 19 and the second defined regions 20 are not provided.

Figure 11:
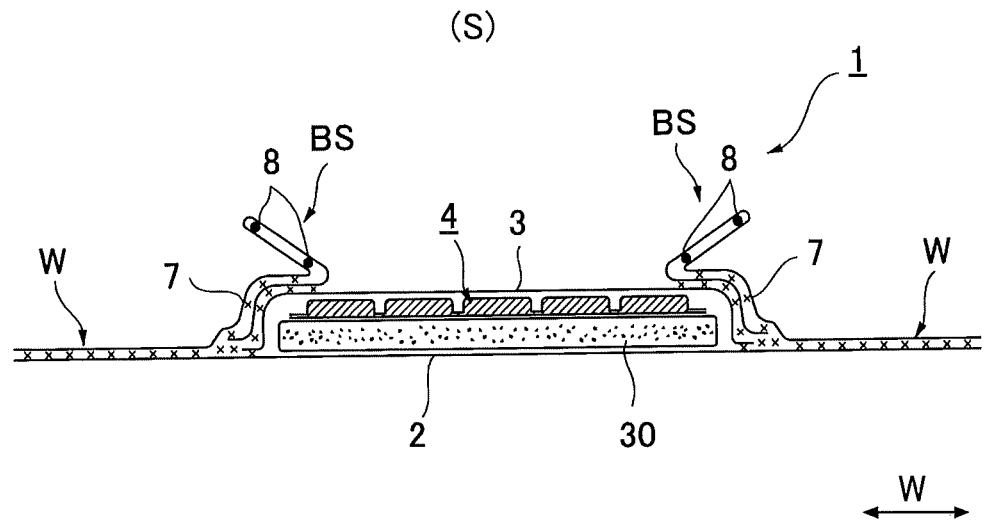
FIG. 11 is a cross-sectional view (No. 1) of a sanitary napkin of a modified example.
Figure 12:
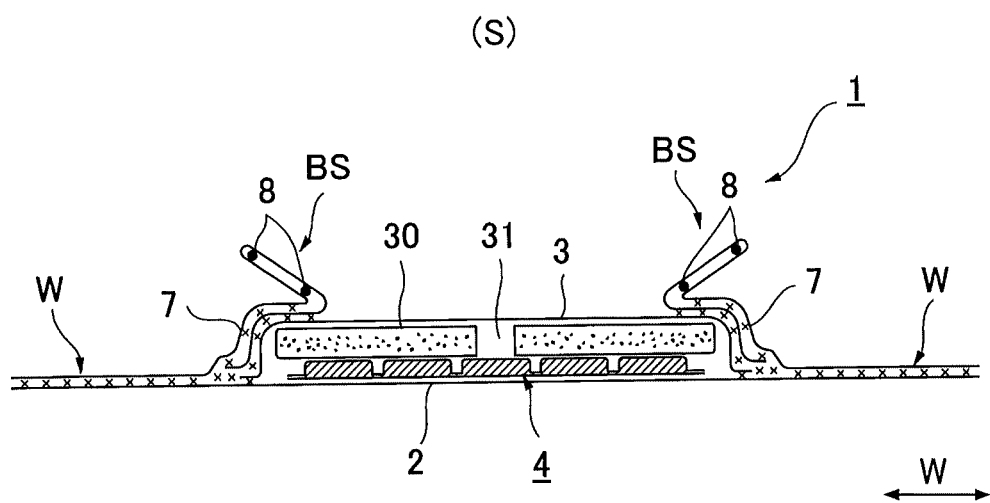
FIG. 12 is a cross-sectional view (No. 2) of a sanitary napkin of a modified example.

FIG. 10 and FIG. 11 are cross-sectional views illustrating modified examples of the sanitary napkin 1 of the embodiment. As illustrated in FIG. 2, only the polymer sheet may be provided between the liquid permeable topsheet 3 and the liquid impermeable backsheet 2. Alternatively, as illustrated in FIG. 11 and FIG. 12, the polymer sheet may be provided as a stacked layer with a fiber assembly layer 30 including an absorbent fiber assembly such as a pulp provided at the non-skin side or at the skin side of the polymer sheet 4. The fiber assembly layer 30 is constituted at least by the absorbent fiber assembly, and a superabsorbent polymer may be mixed.

In FIG. 11, the fiber assembly layer 30 is provided at the non-skin side of the polymer sheet 4, and a stacked layer of the polymer sheet 4 and the fiber assembly layer 30 is provided between the liquid permeable topsheet 3 and the liquid impermeable backsheet 2. With this, body fluid that penetrates the upper polymer sheet 4 is absorbed and retained in the lower fiber assembly layer 30. In this case, as the lower layer sheet 11 constituting the polymer sheet 4, a permeable sheet material may be used.

In FIG. 12, the fiber assembly layer 30 is provided at the skin side of the polymer sheet 4, and a stacked layer of the polymer sheet 4 and the fiber assembly layer 30 are provided between the liquid permeable topsheet 3 and the liquid impermeable backsheet 2. With this, body fluid diffused in the fiber assembly layer 30 can be rapidly absorbed in the polymer sheet 4. At this time, as illustrated in FIG. 12, a slit 31 that penetrates the fiber assembly layer 30 at a center portion in the width direction "W" along the longitudinal direction "L" may be provided. With this, the slit 31 functions as a temporal reserving space of the body fluid, and the body fluid can be diffused in the polymer sheet 4 while diffusing in the longitudinal direction "L" along the slit 31, a diffusion property becomes good and the body fluid can be efficiently and rapidly absorbed in the polymer sheet 4.

When using the stacked layer of the polymer sheet 4 and the fiber assembly layer 30, it is unnecessary to provide the polymer sheet 4 over the entirety of the fiber assembly layer 30, and for example, the polymer sheet 4 may be provided only at a napkin center region including a urine expelling port, or only at a ring region that surrounds the urine expelling port. In this case, the fiber assembly layer 30 is provided over an outer peripheral portion of the sanitary napkin 1 except the peripheral flap portions.

Although not illustrated, the liquid permeable topsheet 3 is not an essential component, and when the upper layer sheet 10 of the polymer sheet 4 functions as a skin contacting surface layer, the liquid permeable topsheet 3 may not be provided. With this, the sanitary napkin 1 can be made further thin, and also cost can be reduced by decreasing the number of materials.

EXAMPLE

The following water absorption test was conducted to examine an effect of the polymer sheet 4 of the embodiment. In the test, as illustrated in FIG. 3, the polymer sheet 4 was used in which the first defined regions 19 and the second defined regions 20 were formed by the first bonded portions 17 and the second bonded portions 18, and the first defined region 19 and the second defined region 20 were configured as the polymer provided regions 13 at which the superabsorbent polymer (manufactured by SDP Global Co., Ltd., EP-2100) was respectively provided. The fabric weight per unit area of the superabsorbent polymer 12 at the polymer provided region 13 was 100 g/m$^2$. The test was conducted by dropping 3 cc of artificial urine on an upper surface of the polymer sheet 4 using an absorption cylinder with a diameter of 25 mm, and measuring absorbing speed (a period necessary for absorbing the artificial urine from the start of dropping) and diffusion area (a diffusion area after 1 minute from end of the absorption) to obtain average values of five times. The artificial urine was constituted by urea: 20 wt %, sodium chloride: 8 wt %, calcium chloride dihydrate: 0.3 wt %, magnesium oxide heptahydrate: 0.8 wt % and pure water: 70.01 wt %.

Results are illustrated in Table 2. Here, the comparative example had a structure in which a superabsorbent polymer was provided between an upper layer sheet and a lower layer sheet where the liquid diffusion sheet 15 is not provided.

TABLE 2

|  | EXAMPLE | COMPARATIVE EXAMPLE |
|---|---|---|
| ABSORPTION SPEED (s) | 1.846 | 1.852 |
| DIFFUSION AREA VERTICAL × LATERAL (mm) | 81 × 62 | 69 × 58 |

As illustrated in Table 2, according to the polymer sheet 4 of the embodiment, compared with the comparative example that does not include the liquid diffusion sheet 15, diffusion area is largely increased, and the urine can be absorbed by the superabsorbent polymer 12 at a wide range.

Although a preferred embodiment and an example have been specifically illustrated and described, it is to be understood that the present invention is not limited to the specifically disclosed embodiment and example and numerous modifications may be made therein without departing from the spirit and scope of the invention as defined by the claims.

Preferred embodiments of the invention are described in the following.

(Clause 1)

There is provided an absorbent article, including: a polymer sheet in which a superabsorbent polymer is provided between an upper layer sheet provided at a skin side, and a lower layer sheet provided at a non-skin side, wherein a polymer provided region at which the superabsorbent polymer is provided, and a polymer non-provided region at which the superabsorbent polymer is not provided are formed in the polymer sheet, wherein a liquid diffusion sheet, that promotes diffusion of body fluid in a plane direction, is stacked to be adjacent to a skin side surface of the lower layer sheet, and wherein the upper layer sheet is bonded with the liquid diffusion sheet under a state that the upper layer sheet contacts the liquid diffusion sheet, at the polymer non-provided region.

With this configuration, the polymer provided region at which the superabsorbent polymer is provided, and the polymer non-provided region at which the superabsorbent polymer is not provided are formed in the polymer sheet. Further, the liquid diffusion sheet, that promotes diffusion of the body fluid in the plane direction, is stacked to be adjacent to the skin side surface of the lower layer sheet. Further, the upper layer sheet is bonded with the liquid diffusion sheet under a state that the upper layer sheet contacts the liquid diffusion sheet at the polymer non-provided region. With this, at the polymer non-provided region, the body fluid permeated from the upper layer sheet to the liquid diffusion sheet can rapidly diffuse in the plane direction by a liquid diffusion action of the liquid diffusion sheet in the plane direction, the body fluid contacts the superabsorbent polymer over a wide range, and the body fluid can be efficiently absorbed. Further, as the body fluid diffused in the plane direction by the liquid diffusion sheet is absorbed from a lower side of the superabsorbent polymer provided in the polymer provided region, the superabsorbent polymer can efficiently absorb the body fluid. Further, as the body fluid diffused in the plane direction by the liquid diffusion sheet is absorbed by the superabsorbent polymer, worsening of fit by increasing in thickness due to swelling of the superabsorbent polymer at a specific narrow region as the body fluid is locally absorbed only by the superabsorbent polymer at the specific narrow region can be prevented.

(Clause 2)

Further, Klemm water absorbency defined by JIS P8141 of the liquid diffusion sheet, by 10 minutes, is greater than or equal to 25 mm, and liquid permeability in a thickness direction of the liquid diffusion sheet may be lower than that of each of the upper layer sheet and the lower layer sheet.

With this configuration, as the liquid diffusion sheet capable of promoting diffusion of the body fluid in the plane direction, a sheet having predetermined Klemm water absorbency, and also whose liquid permeability in the thickness direction is lower than that of each of the upper layer sheet and the lower layer sheet is used. As a material having such a property, for example, a crepe paper, a tissue paper and the like may be exemplified.

(Clause 3)

Further, the polymer sheet may be sectioned into a plurality of first defined regions each of whose inside is the polymer provided region, and second defined regions each of which is positioned at a center of the four adjacent first defined regions and each of whose inside is the polymer non-provided region, each of the first defined regions may be surrounded by bonded portions at least at upper, lower, left and right positions, respectively, each of the bonded portions bonding the upper layer sheet with the liquid diffusion sheet, and the plurality of first defined regions may be aligned in a square lattice form along a longitudinal direction and also a width direction of the absorbent article.

With this configuration, an arrangement pattern of the polymer provided regions and the polymer non-provided regions formed in the polymer sheet is defined, and bonding positions of the upper layer sheet and the liquid diffusion sheet are also defined. Specifically, the plurality of first defined regions in each of which the polymer provided region is provided are aligned in a square lattice form along the longitudinal direction "L" and the width direction "W" of the absorbent article, and each of the second defined regions in which the polymer non-provided region is provided is positioned at a center of the four adjacent first defined regions. Further, bonding positions of the upper layer sheet and the liquid diffusion sheet are at least at the upper, lower, left and right positions of the first defined region. Thus, it is easy for the body fluid to transfer from the upper layer sheet to the liquid diffusion sheet of the polymer sheet via the bonded portions, liquid is easily diffused in the liquid diffusion sheet by the arrangement pattern of the bonded portions in a longitudinal direction and in a lateral direction, and a diffusion property of the body fluid is improved.

The present application is based on and claims the benefit of priority of Japanese Priority Application No. 2015-240050 filed on Dec. 9, 2015, the entire contents of which are hereby incorporated by reference.

NUMERALS

1 . . . sanitary napkin, 2 . . . liquid impermeable backsheet, 3 . . . liquid permeable topsheet, 4 . . . polymer sheet, 7 . . . side non-woven-fabric, 10 . . . upper layer sheet, 11 . . . lower layer sheet, 12 . . . superabsorbent polymer, 13 . . . polymer provided region, 14 . . . polymer non-provided region, 15 . . . liquid diffusion sheet, 16 . . . bonded portion, 17 . . . first bonded portion, 18 . . . second bonded portion, 19 . . . first defined region, 20 . . . second defined region

What is claimed is:

1. An absorbent article, comprising
a polymer sheet in which a superabsorbent polymer is provided between an upper layer sheet provided at a skin side, and a lower layer sheet provided at a non-skin side,
wherein a polymer provided region at which the superabsorbent polymer is provided, and a polymer non-provided region at which the superabsorbent polymer is not provided are formed in the polymer sheet,
wherein a liquid diffusion sheet that promotes diffusion of body fluid in a plane direction is stacked to be adjacent to a skin side surface of the lower layer sheet, the liquid diffusion sheet having a liquid permeability in a thickness direction of the liquid diffusion sheet that is lower than a liquid permeability of each of the upper layer sheet and the lower layer sheet, and wherein the upper layer sheet is bonded with the liquid diffusion sheet under a state that the upper layer sheet contacts the liquid diffusion sheet, at the polymer non-provided region.

2. The absorbent article according to claim 1, wherein Klemm water absorbency defined by JIS P8141 of the liquid diffusion sheet, by 10 minutes, is greater than or equal to 25 mm.

3. The absorbent article according to claim 1, wherein the polymer sheet is sectioned into a plurality of first defined regions each, of whose inside is the polymer provided region, and second defined regions each of which is positioned at a center of the four adjacent first defined regions and each of whose inside is the polymer non-provided region, wherein each of the first defined regions is surrounded by bonded portions at least at upper, lower, left and right positions, respectively, each of the bonded portions bonding the upper layer sheet with the liquid diffusion sheet, and wherein the plurality of first defined regions are aligned in a square lattice fottn along a longitudinal direction and also a width direction of the absorbent article.

4. The absorbent article according to claim 1, wherein the liquid diffusion sheet has a multi-layered structure in which a first sheet that promotes diffusion of the body fluid in the plane direction, and a second sheet whose liquid permeability in the thickness direction is lower than that of each of the upper layer sheet and the lower layer sheet are stacked, and wherein the first sheet and the second sheet are provided in this order from the skin side.

5. The absorbent article according to claim 4, wherein Klemm water absorbency defined by JIS P8141 of the first sheet of the liquid diffusion sheet, by 10 minutes, is greater than or equal to 25 mm.

* * * * *